United States Patent
Shreve et al.

(10) Patent No.: US 9,946,268 B2
(45) Date of Patent: Apr. 17, 2018

(54) PRESSURE RELATED HYSTERESIS MANIPULATION IN A PRESSURIZED FLOW SYSTEM

(71) Applicant: Waters Technologies Corporation, Milford, MA (US)

(72) Inventors: Joshua A. Shreve, Franklin, MA (US); Paul Keenan, Harrisville, RI (US); Steven J. Ciavarini, Natick, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 672 days.

(21) Appl. No.: 14/381,978

(22) PCT Filed: Mar. 7, 2013

(86) PCT No.: PCT/US2013/029539
§ 371 (c)(1),
(2) Date: Aug. 28, 2014

(87) PCT Pub. No.: WO2013/134476
PCT Pub. Date: Sep. 12, 2013

(65) Prior Publication Data
US 2015/0013803 A1     Jan. 15, 2015

Related U.S. Application Data

(60) Provisional application No. 61/607,910, filed on Mar. 7, 2012.

(51) Int. Cl.
*G01N 30/32*     (2006.01)
*G01N 30/86*     (2006.01)
(Continued)

(52) U.S. Cl.
CPC ......... *G05D 7/0623* (2013.01); *B01D 15/163* (2013.01); *F17D 3/00* (2013.01);
(Continued)

(58) Field of Classification Search
CPC .... G05D 7/0623; G05D 7/0617; G05D 16/20; G05D 16/2013; G05D 16/202;
(Continued)

(56) References Cited

U.S. PATENT DOCUMENTS 4,096,746 A * 6/1978 Wilson ............... G01F 1/40
137/501
5,400,678 A   3/1995 Jain et al.
(Continued)

FOREIGN PATENT DOCUMENTS

EP          2402746 A1      1/2012

OTHER PUBLICATIONS

Guiochon G, et al., Fundamental challenges and opportunities for preparative supercritical fluid chromatography. J Chromatogr A. Feb. 25, 2011;1218(8):1037-114.
(Continued)

*Primary Examiner* — Katherine Zalasky
(74) *Attorney, Agent, or Firm* — Womble Bond Dickinson (US) LLP; Deborah M. Vernon; Heath T. Misley

(57) ABSTRACT

Exemplary embodiments of the present disclosure are directed to manipulating pressure-related hysteresis in a pressurized flow system by setting the pressure of the system to a predetermined location in the hysteresis band to advantageously minimize an effect of the pressure related hysteresis on the pressure of the system or to advantageously benefit from the effects of the hysteresis on the pressure of the system.

14 Claims, 11 Drawing Sheets

(51) Int. Cl.
*G05D 7/06* (2006.01)
*B01D 15/16* (2006.01)
*F17D 3/00* (2006.01)
*G05D 16/20* (2006.01)
B01D 15/40 (2006.01)
G01N 30/88 (2006.01)

(52) U.S. Cl.
CPC ......... *G01N 30/32* (2013.01); *G05D 16/2013* (2013.01); *G05D 16/2066* (2013.01); *B01D 15/40* (2013.01); *G01N 30/86* (2013.01); *G01N 30/8658* (2013.01); *G01N 30/8696* (2013.01); *G01N 2030/324* (2013.01); *G01N 2030/326* (2013.01); *G01N 2030/328* (2013.01); *G01N 2030/8804* (2013.01); *Y10T 137/86397* (2015.04)

(58) Field of Classification Search
CPC .................. G05D 16/2066; F17D 3/00; Y10T 137/86397; G01N 30/26; G01N 30/32; G01N 30/28; G01N 30/86; G01N 30/8658; G01N 30/8696; G01N 2030/326; G01N 2030/328; G01N 2030/324; G01N 2030/8804; B01D 15/16; B01D 15/163; B01D 15/40
See application file for complete search history.

(56) References Cited

U.S. PATENT DOCUMENTS

| | | |
|---|---|---|
| 5,998,945 A | 12/1999 | Elliott |
| 2006/0293147 A1 | 12/2006 | Adams et al. |
| 2010/0076664 A1 | 3/2010 | Monros |

OTHER PUBLICATIONS

International Search Report for PCT/US2013/29539 dated May 8, 2013.
Sethna, 'What's Hysteresis?' internet webpage; Jun. 30, 1994; retrieved from http://www.lassp.cornell.edu/sethna/hystersis/WhatIsHysteresis.html on Apr. 17, 2013.

* cited by examiner

PRESSURE RELATED HYSTERESIS MANIPULATION IN A PRESSURIZED FLOW SYSTEM

RELATED APPLICATIONS

This application is a National Stage Application of International Application No. PCT/US2013/029539, filed Mar. 7, 2013, which claims priority to U.S. Provisional Application No. 61/607,910, filing date Mar. 7, 2012. Each of the foregoing applications is incorporated herein by reference in its entirety.

FIELD OF THE TECHNOLOGY

In general, the technology of the present disclosure is directed to methods, processes, systems, and computer readable instructions for controlling pressurization in a pressurized flow system, such as, for example a $CO_2$-based chromatography or a $CO_2$-based extraction system. In particular, the technology of the present disclosure is directed to manipulation of pressure-related hysteresis in a pressurized flow system to advantageous minimize or benefit from pressure-related hysteresis effects on the system.

BACKGROUND

Chromatographic techniques are important tools for the identification and separation of complex samples. The basic principle underlying chromatographic techniques is the separation of a mixture into individual components by transporting the mixture in a moving fluid through a retentive media. The moving fluid is typically referred to as the mobile phase and the retentive media is typically referred to as the stationary phase. The separation of the various constituents of the mixture is based on differential partitioning between the mobile and stationary phases. Differences in components' partition coefficient result in differential retention on the stationary phase, resulting in separation.

Conventionally, the methods of choice for chromatographic separations have been gas chromatography (GC) and liquid chromatography (LC). One major difference between GC and LC is that the mobile phase in GC is a gas, whereas the mobile phase in LC is a liquid. For example, in GC, a supply of inert carrier gas (mobile phase) is continually passed as a stream through a heated column containing porous sorptive media (stationary phase). A sample of the subject mixture is injected into the mobile phase stream and passed through the column, where separation of the mixture is primarily due to the differences in the volatile characteristics of each sample component at the temperature of the column. A detector, positioned at the outlet end of the column, detects each of the separated components as they exit the column. Although GC is typically a sensitive method of analysis, the high temperatures required in GC make this method unsuitable for high molecular weight biopolymers or proteins (heat will denature them), frequently encountered in biochemistry.

Conversely, LC is a separation technique in which the mobile phase is a liquid and does not require volatilization of the sample. Liquid chromatography that generally utilizes small packing particles and moderately high pressure is referred to as high-performance liquid chromatography (HPLC); whereas liquid chromatography that generally utilizes very small packing particles and high pressure is referred to as ultra-high performance liquid chromatography (UHPLC). In HPLC and UHPLC the sample is forced by a liquid at high pressure (the mobile phase) through a column that is packed with a stationary phase composed of irregularly or spherically shaped particles, a porous monolithic layer, or a porous membrane.

Because LC uses liquid as the mobile phase, LC techniques are capable of analyzing higher molecular weight compounds and, in some cases, LC can be used to prepare large scale batches of purified protein(s). However, in contrast, GC techniques are typically more sensitive and readily allow for the separation of single chiral materials. Thus, GC has conventionally been used to isolate and determine the relative purity of a chiral compound, e.g., by determining the enantiomeric excess (% ee) or the diastereomeric excess (% de) of a particular sample. As with most chromatographic techniques, the limiting factor in both GC and LC has been the ability to obtain and/or reproduce pure sample separations, each of which are typically dependent on the apparatus, methods, and conditions employed, e.g., flow rate, column size, column packing material, solvent gradient, etc.

Supercritical Fluid Chromatography is another chromatographic technique, which has typically been used in preparative applications. For every liquid substance there is a temperature above which it can no longer exist as a liquid, no matter how much pressure is applied. Likewise, there is a pressure above which the substance can no longer exist as a gas no matter how much the temperature is raised. These points are called the supercritical temperature and supercritical pressure, and define the boundaries on a phase diagram for a pure substance (FIG. 1). At this point, the liquid and vapor have the same density and the fluid cannot be liquefied by increasing the pressure. Above this point, where no phase change occurs, the substance acts as a supercritical fluid (SF). Thus, SF can be described as a fluid obtained by heating above the critical temperature and compressing above the critical pressure. There is a continuous transition from liquid to SF by increasing temperature at constant pressure or from gas to SF by increasing pressure at constant temperature.

The term SFC, while typically standing for Supercritical Fluid Chromatography, does not require or mean that supercritical conditions are obtained during or maintained throughout the separation. That is, columns do not have to be always operated in the critical region of the mobile phase. For example, in the event that the mobile phase includes a modifier (e.g., $CO_2$ and methanol as a modifier), the mobile phase is often in its subcritical region (e.g., a highly compressed gas or a compressible liquid rather than a supercritical fluid). In fact, as Guiochon et al note in section 2.3 of their review article entitled "Fundamental challenges and opportunities for preparative supercritical fluid chromatography" Journal of Chromatography A, 1218 (2011) 1037-1114: "It is obvious that SFC has very often been and still is run under subcritical conditions." Thus, the term SFC is not limited to processes requiring supercritical conditions.

Because SFC typically uses $CO_2$, SFC processes are inexpensive, innocuous, eco-friendly, and non-toxic. There is typically no need for the use of volatile solvent(s) (e.g., hexane). Finally, the mobile phase in SFC processes (e.g., $CO_2$ together with any modifier/additive as a SF, highly compressed gas, or compressible liquid) typically have higher diffusion constants and lower viscosities relative to liquid solvents. The low viscosity means that pressure drops across the column for a given flow rate is greatly reduced. The increased diffusivity means longer column length can be used.

SUMMARY

Exemplary embodiments of the present disclosure are directed methods, apparatuses, systems, and computer readable storage mediums configured to manipulate pressure-related hysteresis in a pressurized flow system by setting the pressure of the system to a predetermined location in the hysteresis band to advantageously minimize an effect of the pressure related hysteresis on the pressure of the system or to advantageously benefit from the effects of the hysteresis on the pressure of the system. Embodiments of the pressurized flow system can be implemented as a $CO_2$-based chromatography system in which a mobile phase is passed through a stationary phase, sample components of a sample in the mobile phase are separated, and one or more characteristics of the sample components are detected.

In one embodiment, a pressurized flow system having pressure related hysteresis is disclosed. The system includes a valve and a processing device. The valve is configured to adjust the pressure of the system. The controller is in communication with the valve to adjust the pressure of the system to a predetermined location with respect to a pressure related hysteresis band.

In another embodiment, a method of manipulating pressure-related hysteresis in a pressurized flow system is disclosed. The method includes pressurizing the system and adjusting a pressure of the system by a first quantity that exceeds a pressure range associated with a pressure related hysteresis band to set the pressure to a first predetermined location in the hysteresis band.

In another embodiment, a non-transitory computer readable storage medium stores instructions to be executed by a processing device is disclosed. Execution of the instructions causes the processing device to shift a pressure related hysteresis band by a first quantity in response to a first command signal, shift the pressure related hysteresis band by a second quantity after a predetermined time period elapsed in which a disturbance to the pressure of the system occurred. The second quantity exceeding the pressure range associated with the hysteresis band to set the pressure of the system to an upper boundary of the hysteresis band. Execution of the instructions by the processing device can further cause the processing device to increase the pressure of the system based on a predetermined gradient.

In some embodiments, the valve can be controlled to adjust the pressure by a quantity that exceeds a pressure range associated with the hysteresis band to shift the hysteresis band and to set the pressure of the system at a predetermined location in the hysteresis band. The pressure range associated with the hysteresis band can have an upper boundary and a lower boundary, and the valve can be controlled to adjust the pressure to be greater than the upper boundary or less than the lower boundary. In some embodiments, the pressure range associated with the hysteresis band can be substantially constant so that when the hysteresis band is shifted, the upper boundary and lower boundary shift by a substantially identical pressure value.

In some embodiments, the valve to adjust the pressure of the system to a higher pressure to exceed the upper boundary of the pressure range and to shift the upper boundary of the hysteresis band to the higher pressure.

In some embodiments, the valve can be adjusted to adjust the pressure of the system to a lower pressure to reduce the pressure of the system beyond the lower boundary of the pressure range and to shift the lower boundary of the hysteresis band to the lower pressure.

In some embodiments, the valve can be controlled to reduce the pressure of the system from a first pressure value that is greater than the lower boundary to a second pressure value that is less than the lower boundary to shift the hysteresis band so that the lower boundary is substantially equal to the second pressure value.

In some embodiments, the valve can be controlled to increase the pressure of the system from the second pressure value to a third pressure value that is greater than the upper boundary to shift the hysteresis band so that the upper boundary is substantially equal to the third pressure value. The first and third pressure values can be substantially equal.

In some embodiments, the valve can be controlled to transition from the second pressure value to the third pressure value after a predetermined time period has elapsed.

In some embodiments, the valve can be adjusted to set the pressure to at least one of an upper boundary, a lower boundary, and a center of the hysteresis band.

In some embodiments, the pressure is set at an upper boundary of the hysteresis band and to an initial pressure value associated with a pressure gradient before a sample is injected into the system.

In some embodiments, the pressure is decreased to shift the upper boundary of the hysteresis band to pre-injection pressure value that is less than the initial pressure value, the sample is injected into the system, the pressure is set at the upper boundary of the hysteresis band and to the initial pressure value after the injection, and the pressure of the system is increase according to the pressure gradient from the initial pressure value.

In some embodiments, the valve is controlled using a decaying periodic signal having converging upper and lower peaks. The upper boundary of the hysteresis band can shift to the pressure set by the upper peaks and the lower boundary of the hysteresis band can shift to the pressure set by the lower peaks in an alternating sequence until a peak-to-peak amplitude of the periodic signal decays to be less than the pressure range of the hysteresis band. The pressure of the system can be positioned approximately at a center of the hysteresis band after the peak-to-peak amplitude of the periodic signal decays to be less than the pressure range.

In some embodiments, the valve comprises an actuator in communication with a valve member and the actuator adjusts a position of the valve member to adjust the pressure of the system. In some embodiments, the actuator and valve member comprises a dynamic pressure regulator of the system.

In some embodiments, the actuator can be a solenoid and/or a voice coil.

In some embodiments, the valve in response to a command signal.

In some embodiments, the system can be a $CO_2$-based chromatography system.

One or more embodiments feature methods or processes directed to providing improved control over pressure in a pressurized flow system. For example, in an embodiment, the methods or processes provide improved pressure control for a back pressure regulator in a $CO_2$-based chromatographic system. In particular the methods or processes provide an advantage of controlling a location in the hysteresis band in the back pressure regulator to improve "takeoff" or initial/response behavior at the beginning of a pressure gradient and performance of isobaric runs. Any combination or permutation of embodiments is envisioned.

BRIEF DESCRIPTION OF THE DRAWINGS

The foregoing and other features and advantages provided by the present disclosure will be more fully understood from the following description of exemplary embodiments when read together with the accompanying drawings, in which.

DETAILED DESCRIPTION

Figure 1:
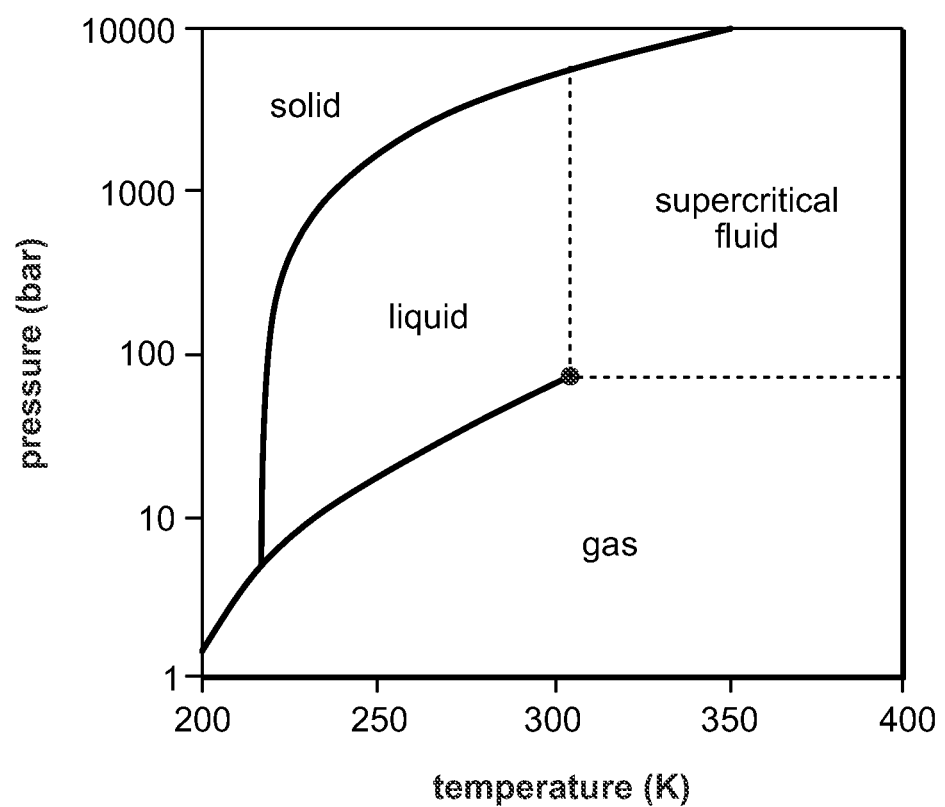
FIG. 1 is an exemplary graph of the physical state of a substance in relation to a temperature and pressure associated with the substance.

SFC can be adapted as a hybrid between HPLC and GC apparatuses, where the predominant modification is replacement of either the liquid or gas mobile phase with a supercritical fluid (or near supercritical fluid) mobile phase, such as with $CO_2$. In SFC, the mobile phase is initially pumped as a liquid or gas and is brought into the supercritical region by heating or pressurizing the mobile phase above its supercritical temperature/pressure prior to entry into a column. As the mobile phase passes through an injection valve, the sample is introduced into the supercritical stream, and the mixture is then transferred into a column. The mixture passes through the column (at supercritical or liquid state) and into the detector.

In general, the mobile phase in SFC processes have the ability to act both as substance carriers (like the mobile phases in GC), and dissolve substances readily (like the solvents used in LC). In addition to generally having lower viscosities and better diffusion profiles similar to those of certain gases, the mobile phase in SFC processes also generally have high densities and dissolving capacities similar to those of certain liquids. For example, SFs' high densities (0.2-0.5 gm/cm$^3$) provide for their remarkable ability to dissolve large, non-volatile molecules, e.g., supercritical or near supercritical $CO_2$ readily dissolves n-alkanes, di-n-alkyl phthalates, and polycyclic and aromatic compounds. Since the diffusion of solutes in a SFC mobile phase is about ten times greater than that in liquids (about three times less than in gases), this results in a decrease in resistance to mass transfer in the column and allows for fast high resolution separation. Also, the solvation strength of the mobile phase in SFC processes is directly related to the fluid density. Thus, the solubility of solids can be easily manipulated by making slight changes in temperatures and pressures.

Another important property of the mobile phase in SFC processes is that it provides high resolution chromatography at much lower temperatures. For example, an analyte dissolved in supercritical $CO_2$ can be recovered by reducing the pressure and allowing the sample to evaporate under ambient laboratory conditions. This property is useful when dealing with thermally unstable analytes, such as high molecular weight biopolymers or proteins. The combination of one or more mechanical or column changes to an SFC instrument (e.g., a $CO_2$-based chromatography instrument) coupled with the inherent properties of the SFC itself, allows for the separation of both chiral and achiral compounds, and has become increasingly predominant in the field of preparatory separations for drug discovery and development. Despite considerable advances in SFC technology, there is a need to develop innovative methods and apparatuses that improve the use of SFC. Controlling and stabilizing the pressure in an SFC instrument by one or more process and/or improving one or more of the instrumental characteristics of the system, may lead to, amongst others, improved compound separation and efficiency.

For example, better resolution and increased flow rate would decrease cycle times (i.e., shorter cycle times) and allow for improved separation of both chiral and achiral compounds, and lead to an overall increase in laboratory efficiency; increased speed and throughput would decrease the amount of solvent and cost(s) associated with SFC; and the ability to further integrate SFC with other detection methods, such as Mass Spectrometry (MS), Flame Ionization Detectors (FID), and Ultraviolet/Visible (UV) detectors, would improve the mainstream use of SFC using a mobile phase including $CO_2$ as an eco-friendly, yet effective, alternative method for the fast, complete, and sensitive analysis of analytes.

Exemplary embodiments of the present disclosure are directed to manipulating pressure-related hysteresis in a pressurized flow system, such as a $CO_2$-based chromatography system or other pressured flow systems. Exemplary embodiments, can implement one or more procedures or processes for setting the pressure of the system to a predetermined location in the hysteresis band to advantageously minimize the effects of the hysteresis on the pressure of the system or to advantageously benefit from the effects of the hysteresis on the pressure of the system. As one example, a sample detection run can be implemented with a pressure gradient for which it is advantageous to minimize the effects of the hysteresis. For such runs, the initial pressure associated with the pressure gradient can be set to an upper or lower boundary of the hysteresis band. As another example, a sample detection run can be implemented for which a substantially constant pressure is advantageous. For such runs, the pressure of the system can be set approximately to a center of the hysteresis band.

As used herein, the terms "downstream" and "upstream" refer to relative locations in a system flow, wherein upstream refers to being associated with an earlier portion of the system flow compared to a later portion of the system flow and downstream refers to being associated with a later portion of the system flow compared to an earlier portion of the system flow.

Figure 2:
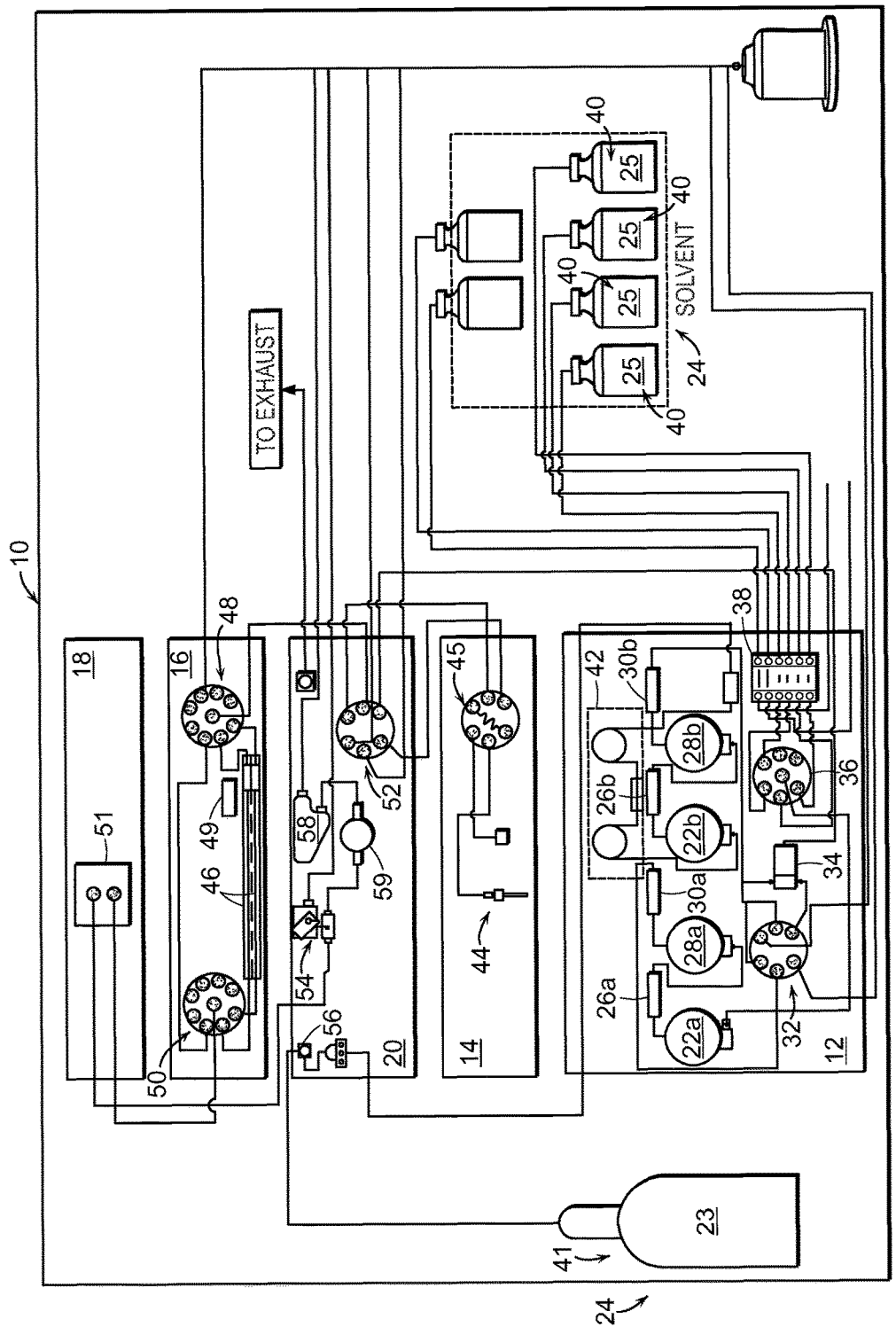
FIG. 2 is a block diagram of an exemplary pressurized flow system.

FIG. 2 is a block diagram of an exemplary pressurized flow system, which in the present embodiment is implemented as a $CO_2$-based chromatography system 10. While the present embodiment is illustrative of a $CO_2$-based chromatography system, those skilled in the art will recognize that exemplary embodiments of the present disclosure can be implemented as other pressurized flow systems and that one or more system components of the present disclosure can be implemented as components of other pressurized systems. The system 10 can be configured to detect sample components of a sample using chromatographic separation in which the sample is introduced into a mobile phase that is passed through a stationary phase. The system 10 can include one or more system components for managing and/or facilitating control of the physical state of the mobile phase, control of the pressure of the system 10, introduction of the sample to the mobile phase, separation of the sample into components, and/or detection of the sample components, as well as venting of the sample and/or mobile phase from the system 10.

Figure 3:
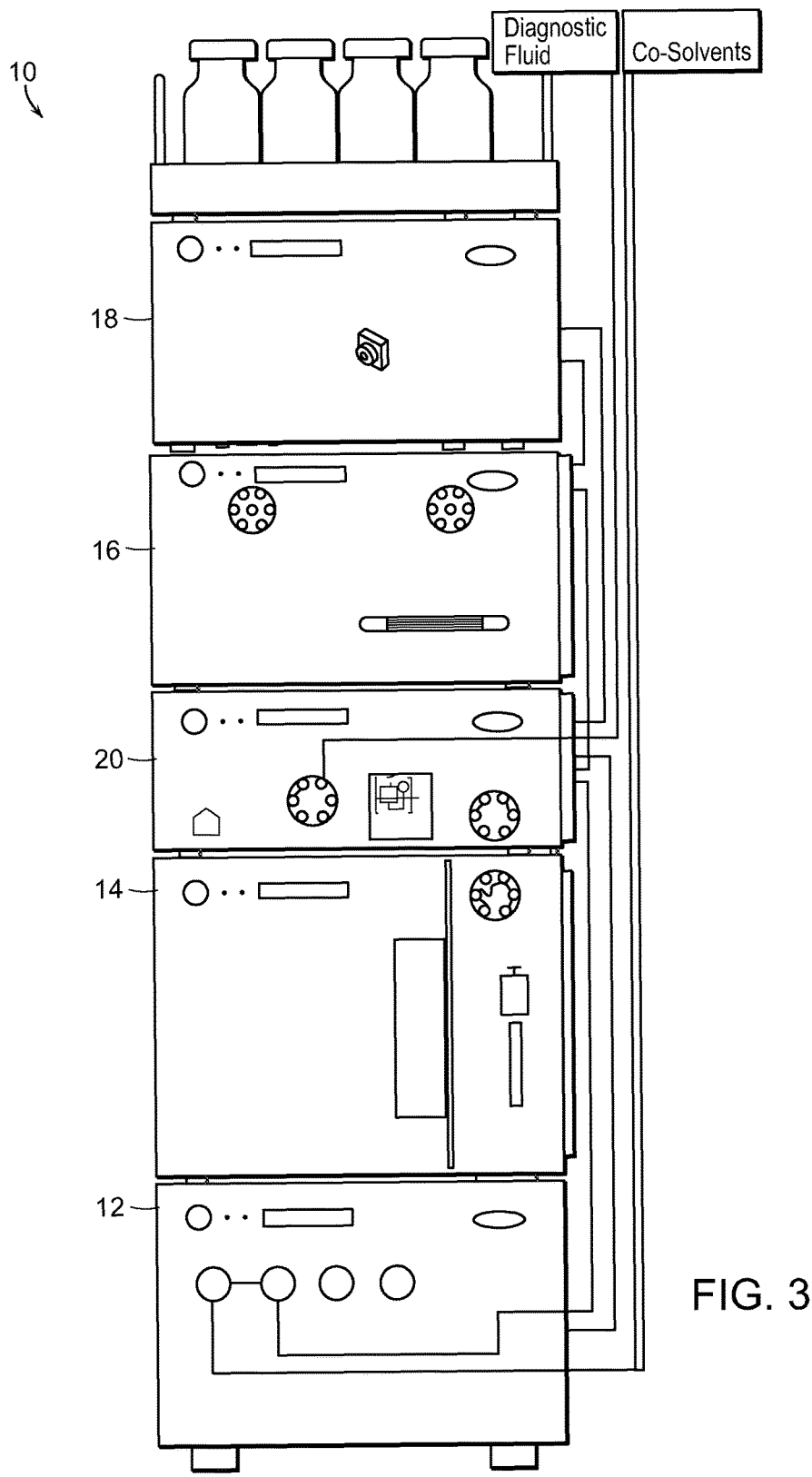
FIG. 3 is a block diagram of an exemplary arrangement of an embodiment of the system of FIG. 2.
Figure 4:
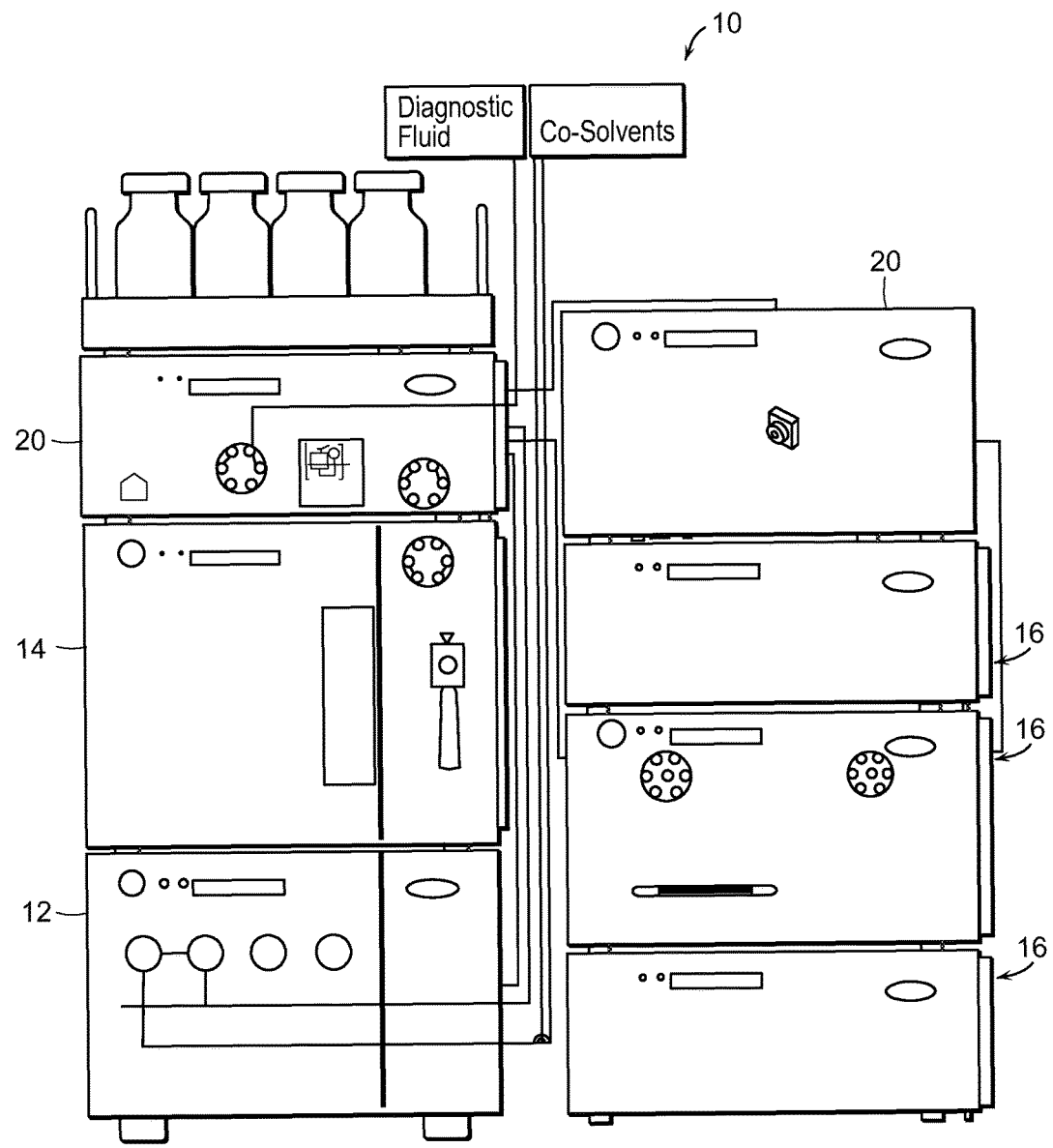
FIG. 4 is a block diagram of another exemplary arrangement of an embodiment of the system of FIG. 2.

In the present embodiment, the system 10 can include a solvent delivery system 12, a sample delivery system 14, a sample separation system 16, a detection system 18 (e.g., PDA detector), and system/convergence manager 20. In some embodiments, the system components can be arranged in one or more stacks. As one example, in one embodiment, the system components of the system 10 can be arranged in a single vertical stack (FIG. 3). As another example, the system components of the system 10 can be arranged in multiple stacks (FIG. 4). Those skilled in the art will recognize that other arrangements of the components of the system 10 are possible. Furthermore, while embodiments of the system 10 have been illustrated as including system components 12, 14, 16, 18, and 20, those skilled in the art will recognize that embodiments of the system 10 can be implemented as a single integral unit, that one or more components can be combined, and/or that other configurations are possible.

The solvent delivery system 12 can include one or more pumps 22a, 22b configured to pump one or more solvents 24, such as mobile phase media 23 (e.g., carbon dioxide) and/or modifier media 25 (i.e., a co-solvent, such as e.g., methanol, ethanol, 2-methoxyethanol, isopropyl alcohol, or dioxane), through the system 10 at a predetermined flow rate. For example, the pump 22a can be in pumping communication with the modifier media 25 to pump the modifier media 25 through the system 10, and the pump 22b can be in pumping communication with the mobile phase media 23 to pump the mobile phase media 23 through the system 10. An output of the pump 22a can be monitored by a transducer 26a and an output of the pump 22b can be monitored by a transducer 26b. The transducers 26a, 26b can be configured to sense the pressure and/or flow rate associated with the output of the solvent 24 from the pumps 22a, 22b, respectively.

The outputs of the pumps 22a, 22b can be operatively coupled to an input of accumulators 28a and 28b, respectively. The accumulators 28a and 28b are refilled by the outputs of the pumps 22a and 22b, respectively, and can contain an algorithm to reduce undesired fluctuations in the flow rate and/or pressure downstream of the pumps 22a and 22b, which can cause detection noise and/or analysis errors on the system 10. An output of the accumulator 28a can be monitored by a transducer 30a and an output of the accumulator 28b can be monitored by a transducer 30b. The transducers 30a, 30b can be configured to sense pressure and/or flow rate at an output of the accumulators 28a, 28b, respectively. The outputs of the accumulators 28a, 28b can be operatively coupled to a multiport valve 32, which can be controlled to vent the solvent 24 (e.g., mobile phase media 23 and modifier media 25) being pumped by the pumps 22a, 22b and/or to output the solvent 24 to a mixer 34. The mixer 34 can mix the modifier media 25 and the mobile phase media 23 output from the pumps 22a, 22b, respectively (e.g., after first passing through the accumulators 28a, 28b) and can output a mixture of the mobile phase media 23 and the modifier media 25 to form a solvent stream (i.e., mobile phase) that flows through the system 10. The output of the mixer 34 can be operatively coupled to the system/convergence manager 20 as discussed in more detail below.

In exemplary embodiments, the solvent delivery system 12 can include a multiport solvent selection valve 36 and/or a degasser 38. The solvent selection valve 36 and/or the degasser 38 can be operatively disposed between an input of the pump 22a and solvent sources, e.g., containers 40, such that the solvent selection valve 36 and/or the degasser 38 are positioned upstream of the pump 22a. The solvent selection valve 36 can be controlled to select the modifier media 23 to be used by the system 10 from one or more solvent containers 40 and the degasser 38 can be configured to remove dissolved gases from the media modifier 23 before the media modifier 23 is pumped through the system 10.

In exemplary embodiments, the solvent delivery system 12 can include a pre-chiller 42 disposed between an input of the pump 22b and a solvent source, e.g., container 41, such that the pre-chiller is disposed upstream of the input to the pump 22b and downstream of the solvent container 41. The pre-chiller 42 can reduced the temperature of the mobile phase media 23 before it is pumped through the system 10 via the pump 22b. In the present embodiment, the mobile phase media 23 can be carbon dioxide. The pre-chiller can decrease the temperature of the carbon dioxide so that the carbon dioxide is maintained in a liquid state (i.e., not a gaseous state) as it is pumped through at least a portion of the system 10. Maintaining the carbon dioxide in a liquid state can facilitate effective metering of the carbon dioxide through the system 10 at the specified flow rate.

The pumps 22a and 22b can pump the solvent 24 through the system 10 to pressurize the system 10 to a specified pressure, which may be controlled, at least in part, by the system/convergence manager 20. In exemplary embodiments, the system 10 can be pressurized to a pressure between about 700 psi and about 18,000 psi or about 1,400 psi and about 8,000 psi. In one embodiment, the system 10 can be pressurized to a pressure of about 6,000 psi. By pressurizing the system 10 at these pressure levels (such as those pressure levels described above), the solvent stream (i.e., mobile phase) can be maintained in a liquid state before transitioning to a supercritical fluid state or near supercritical state (e.g., highly-compressed gas or compressible liquid)

for a chromatographic separation in a column, which can be accomplished by raising the temperature of the pressurized solvent stream.

The sample delivery system 14 can select one or more samples to be passed through the system 10 for chromatographic separation and detection. The sample delivery system 14 can include a sample selection and injection member 44 and a multi-port valve 45. The sample selection and injection member 44 can include a needle through which the sample can be injected into the system 10. The multiport valve 45 can be configured to operatively couple the sample selection and injection member 44 to an input port of the system/convergence manager 20.

The sample separation system 16 can receive the sample to be separated and detected from the sample delivery system 14, as well as the pressurized solvent stream from the solvent delivery system 12, and can separate components of the sample passing through the system 10 to facilitate detection of the samples using the detection system 18. The sample separation system 16 can include one or more columns 46 disposed between an inlet valve 48 and an outlet valve 50. The one or more columns 46 can have a generally cylindrical shape that forms a cavity, although one skilled in the art will recognize that other shapes and configurations of the one or more columns is possible. The cavity of the columns 46 can have a volume that can at least be partially filled with retentive media, such as hydrolyzed silica, such as $C_8$ or $C_{18}$, or any hydrocarbon, to form the stationary phase of the system 10 and to promote separation of the components of the sample. The inlet valve 48 can be disposed upstream of the one or more columns can be configured to select which of the one or more columns 46, if any, receives the sample. The outlet valve 50 can be disposed downstream of the one or more columns 46 to selective receive an output from the one or more columns 46 and to pass the output of the selected one or more columns 46 to the detection system 18. The columns 46 can be removeably disposed between the valves 48, 50 to facilitated replacement of the one or more columns 46 new columns after use. In some embodiments, multiple sample separation systems 16 can be included in the system 10 to provide an expanded quantity of columns 46 available for use by the system 10 (FIG. 4).

In exemplary embodiments, the sample separation system 16 can include a heater 49 to heat the pressurized solvent stream 24 prior and/or while the pressured solvent stream 24 passes through the one or more columns 46. The heater 49 can heat the pressurized solvent stream to a temperature at which the pressured solvent transition from a liquid state to a supercritical fluid state so that the pressurized solvent stream passes through the one or more columns 46 as a supercritical fluid.

Referring again to FIG. 2, the detection system 18 can be configured to receive components separated from a sample by the one or more columns 46 and to detect a composition of the components for subsequent analysis. In an exemplary embodiment the detection system 18 can include one or more detectors 51 configured to sense one of more characteristics of the sample components. For example, in one embodiment, the detectors 51 can be implemented as one or more photodiode arrays.

The system/convergence manager 20 can be configured to introduce a sample from the sample delivery system 14 into the pressurized solvent stream flowing from the solvent delivery system 12 and to pass the solvent stream and sample to the sample separation system 16. In the present embodiment, the system/convergence manager 20 can include a multiport auxiliary valve 52 which receives the sample injected by the sample delivery system 14 through a first inlet port and the pressurized solvent stream from the solvent delivery system 12 through a second inlet port. The auxiliary valve 52 can mix the sample and the solvent stream and output the sample and solvent stream via an outlet port of the multiport auxiliary valve 52 to an inlet port of the inlet valve 48 of the sample separation system 16.

The system/convergence manager 20 can also be configured to control the pressure of the system 10 and to facilitate cooling, heating, and/or venting of the solvent from the system 10, and can include a vent valve 54, a shut off valve 56, a back pressure regulator 58, and a transducer 59. The vent valve 54 can be disposed downstream of the detection system 18 can be configured to decompress the system 10 by venting the solvent from the system 10 after the solvent has passed through the system 10. The shut off valve 56 can be configured to disconnect the solvent supply from the inlet of the pump 22b of the solvent delivery system to prevent the solvent from being pumped through the system 10.

The back pressure regulator 58 can control the back pressure of the system 10 to control the flow of the mobile phase and sample through the column, to maintain the mobile phase in the supercritical fluid state (or, in some embodiments, in a near supercritical state, such as, a highly-compressed gas or compressible liquid) as the mobile phase passes through the one or more columns 46 of the sample separation system 16, and/or to prevent the back pressure from forcing the mobile phase reversing its direction a flow through the one or more columns 46. Embodiments of the back pressure regulator 58 can be configured to regulate the pressure of the system 10 so that the physical state of the solvent stream (i.e., mobile phase) does not change uncontrollably upstream of and/or within the back pressure regulator 58. The transducer 59 can be a pressure sensor disposed upstream of the back pressure regulator 58 to sense a pressure of the system 10. The transducer 59 can output a feedback signal to a processing device which can process the signal to control an output of an actuator control signal from the processing device.

Figure 5:
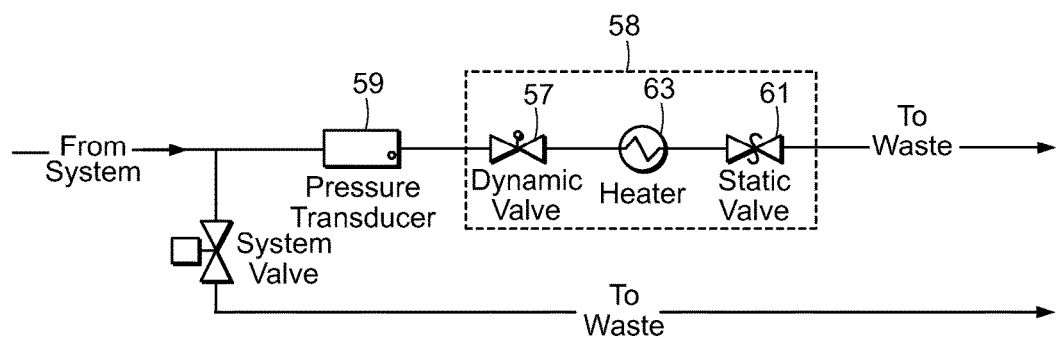
FIG. 5 is a flow diagram of a mobile phase through a system manager portion of the an exemplary embodiment of the pressurized flow system.

In exemplary embodiments, as shown in FIG. 5, the back pressure regulator 58 can include a dynamic pressure regulator 57, a static pressure regulator 61, and a heater 63. The static pressure regulator 61 can be configured to maintain a predetermined pressure upstream of the back pressure regulator 58. The dynamic pressure regulator 57 can be disposed upstream of the static pressure regulator 61 and can be configured to set the system pressure above the predetermined pressure maintained by the static regulator 61. The heater 63 can be disposed downstream of the dynamic pressure regulator 57 and can be disposed in close proximity to the static pressure regulator 61 to heat the solvent stream as it passes through the static pressure regulator 61 to aid in control of the physical state of the solvent as it passes through the static pressure regulator. The structure, function, and/or operation of the back pressure regulator 58, static pressure regulator, and/or dynamic regulator are described in more detail below.

In summary, an exemplary operation of the $CO_2$-based chromatography system 10 can pump mobile phase media 23 and modifier media 25 at a specified flow rate through the system 10 as a solvent stream (i.e., mobile phase) and can pressurize the system 10 to a specified pressure so that the solvent stream maintains a liquid state before entering the sample separation system 16. A sample can be injected into the pressurized solvent stream by the sample delivery system 14, and the sample being carried by the pressurized solvent stream can pass through the sample separation system 16, which can heat the pressurized solvent stream to transition the pressurized solvent stream from a liquid state to a supercritical fluid state. The sample and the supercritical fluid solvent stream can pass through at least one of the one or more columns 46 in the sample separation system 16 and the column(s) 46 can separate components of the sample from each other. The separated components can pass the separated components to the detection system 18, which can detect one or more characteristics of the sample for subsequent analysis. After the separated sample and solvent pass through the detection system 18, the solvent and the sample can be vented from the system 10 by the system/convergence manager 20.

In other embodiments, the $CO_2$-based chromatography system 10 described herein can also be used for preparatory methods and separations. Typical parameters, such as those described above, may be manipulated to achieve effective preparatory separations. For example, the system 10 described herein confers the benefit of exerting higher flow rates, larger columns, and column packing size, each of which contributes to achieving preparatory separation and function, while maintaining little or no variability in overall peak shape, peak size, and/or retention time(s) when compared to respective analytical methods and separations thereof. Thus, in one embodiment, the present disclosure provides $CO_2$-based chromatography systems, which are amendable to preparatory methods and separations with high efficiency and correlation to analytical runs.

Figure 6:
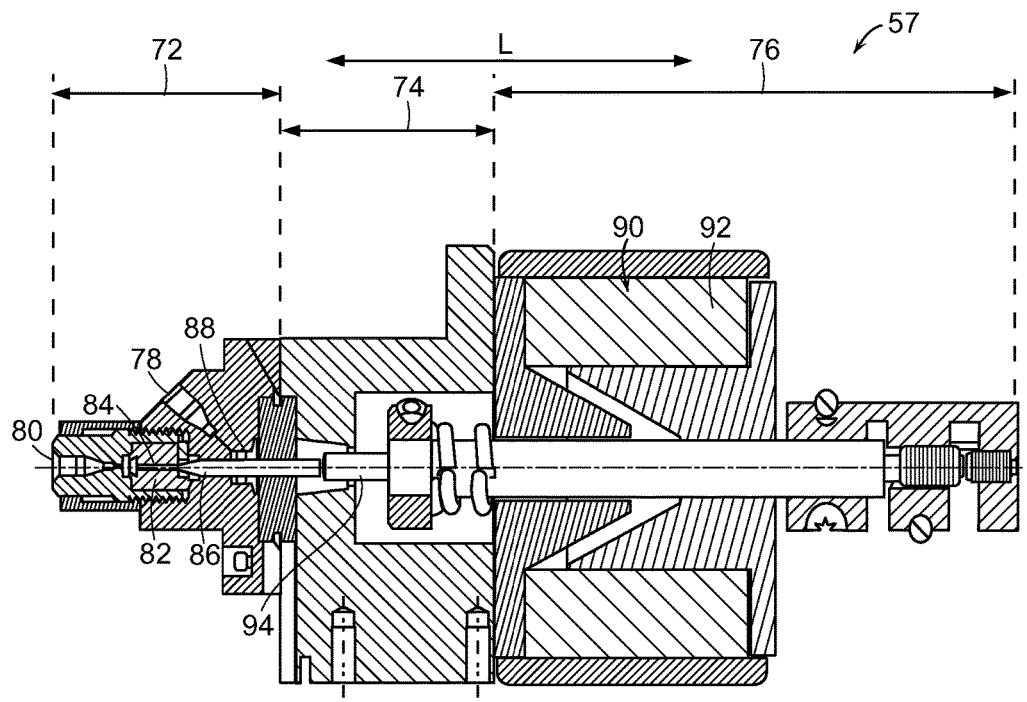
FIG. 6 is a cross-sectional view of a valve assembly for an exemplary dynamic pressure regulator in an exemplary embodiment of the pressurized system.

FIG. 6 is a cross-sectional view of an exemplary embodiment of a dynamic pressure regulator 57 along a longitudinal axis L of the dynamic pressure regulator. The dynamic pressure regulator 57 can be implemented as a valve assembly that includes a proximal head portion 72, an intermediate body portion 74, and a distal actuator portion 76. The head portion 72 of the valve assembly can include an inlet 78 to receive the pressurized solvent stream and an outlet 80 through which the pressurized solvent stream is output such that the solvent stream flows through the head portion from the inlet 78 to the outlet 80. A seat 82 can be disposed within the head portion 72 and can include a bore 84 through which the solvent stream can flow from the inlet 78 to the outlet 80 of the head.

A needle 86 extends into the head portion 72 from the body portion 74 of the valve assembly through a seal 88. A position of the needle 86 can be controlled with respect to the seat 82 to selectively control a flow of the solvent stream from the inlet 78 to the outlet 80. In exemplary embodiments, the position of the needle 86 can be used to restrict the flow through the bore 84 of the seat 82 to increase the pressure of the system 10 and can selectively close the valve by fully engaging the seat 82 to interrupt the flow between the inlet 78 and the outlet 80. By controlling the flow of the solvent stream through the head portion based on the position of the needle 86, the pressure of the system 10 can be increased or decreased. For example, the pressure of the system 10 can generally increase as the needle 86 moves towards the seat 82 along the longitudinal axis L and can generally decrease as the needle 86 moves away from the seat 82 along the longitudinal axis L.

The actuator portion 76 can include an actuator 90, such as a solenoid, voice coil, and/or any other suitable electromechanical actuation device. In the present embodiment, the actuator 90 can be implemented using a solenoid having a main body 92 and a shaft 94. The shaft 94 can extend along the longitudinal axis L and can engage a distal end of the needle 86 such that the needle 86 and shaft can form a valve member. A position of the shaft 94 can be adjustable with respect to the main body 92 along the longitudinal axis L and can be controlled by a coil (not shown) of the main body 92, which generates a magnetic field that is proportional to an electric current passing through the coil and a load applied to the shaft. The electric current passing through the coil can be controlled in response to an actuator control signal received by the actuator 90. In some embodiments, the actuator control signal can be a pulse width modulated (PWM) signal and/or the actuator control signal can be determined, at least in part, by the feedback signal of the pressure transducer 59.

The position of the shaft 94 can be used to move the needle 86 towards or away from the seat 82 to increase or decrease pressure, respectively. In exemplary embodiments, a position of the shaft 94, and therefore a position of the needle 86 with respect to the seat 82 can be controlled and/or determined based on an amount of electric current flowing through the solenoid. For example, the greater the electrical current the closer to the needle 86 and shaft 94 are from the seat and the lower the pressure is in the system 10. The relationship between a position of the shaft 94 and the electric current flowing through the coil can be established through characterization of the actuator 90. The force imposed by the load on the solenoid can be proportional to the magnetic field. Similarly, the magnetic field can be proportional to the electric current flowing through the coil of the solenoid. For embodiments in which the actuator control signal is implemented as a PWM control signal, the pressure through the regulator 57 (e.g., force balance between needle 86 and shaft 94) can be set by a correlation to the duty cycle of the PWM control signal, e.g., a percentage of the duty cycle corresponding to an "on" state.

Figure 7:
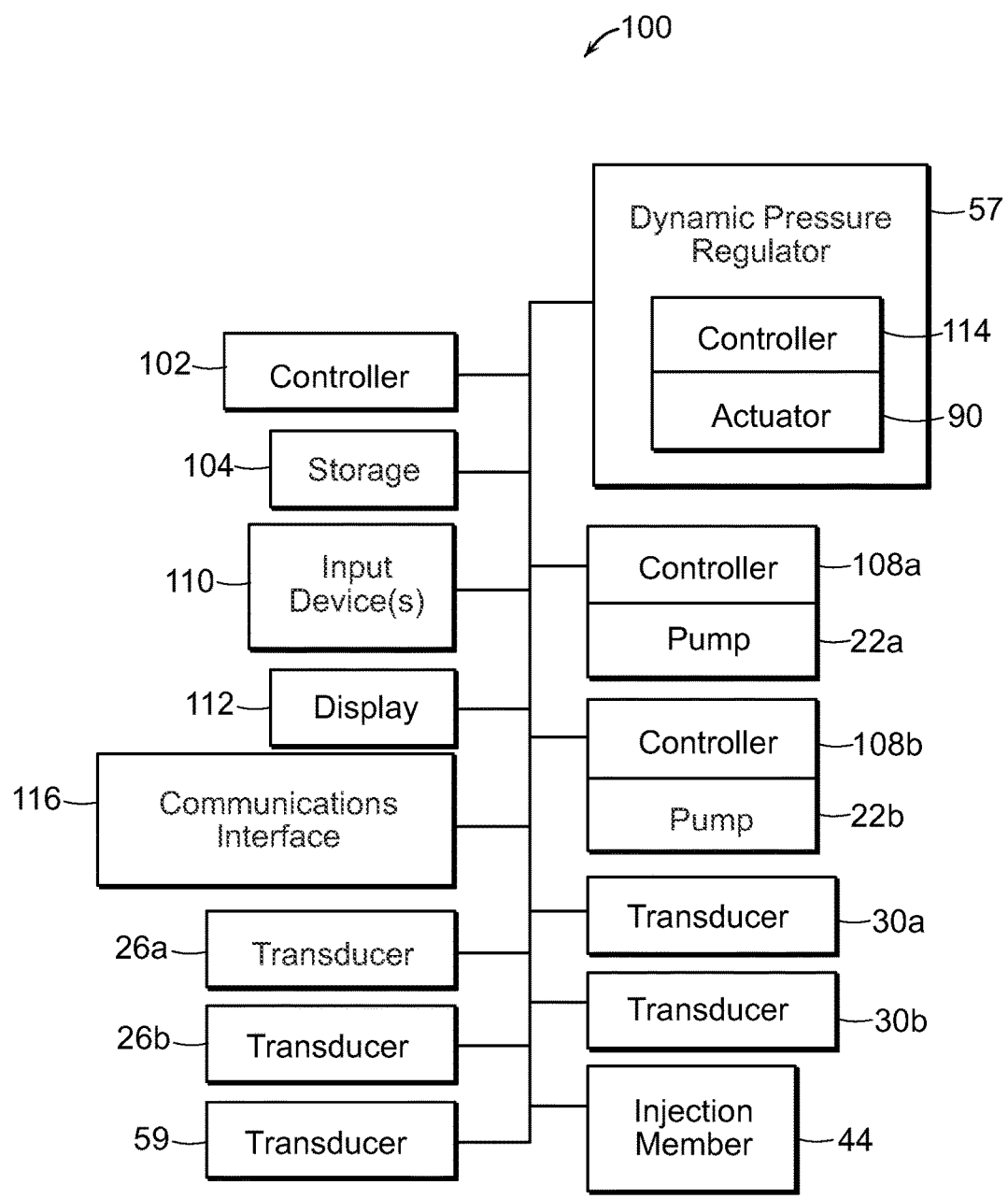
FIG. 7 is a block diagram of an exemplary control system that can be implemented to control an operation of an exemplary embodiment of the pressurized flow system.

FIG. 7 is a block diagram of an exemplary control system 100 that can be implemented to control the pressure of the system 10. The control system 100 can include a controller 102 in electrical communication with a storage device 104 (e.g., memory and/or other computer-readable storage mediums). The controller 102 can be implemented as a microcontroller, microprocessor, field programmable gate array (FPGA), and/or other processing devices. The storage 104 can be implemented as non-transitory computer readable medium including, for example, magnetic storage disks, optical disks, flash or solid state storage, and/or any other nonvolatile or volatile storage medium including random access memory, such as DRAM, SRAM, EDO RAM, MRAM, and the like. The storage 106 can store information corresponding to the system 10 and/or components thereof. The storage 106 can also store instructions that are executable by the controller 102 to control an operation of system 10 including an operation of the dynamic back pressure regulator 57. The controller 102 can also be in communication with one or more of the pumps 22a, 22b, one or more of the transducers 26a, 26b, 30a, 30b, 59, the injection member 44, the dynamic pressure regulator 57, input devices 110, and/or a display 112. In this embodiment, the pumps, 22a, 22b can be associated with pump controllers 108a, 108b, respectively, and the actuator 90 of the dynamic pressure regulator 57 can be associated with an actuator controller 114. The controller 102 can receive signals from and/or transmit signals to the transducers 26a, 26b, 30a, 30b, 59, the injection member 44, the pump controllers 108a, 108b, one or more input devices 110, such as a keyboard, mouse, or other suitable input devices, the display 112, and the actuator controller 114, and/or other devices, such as other controllers (e.g., processing devices), computing devices (e.g., a Laptop, PC, mainframe), networked devices (e.g., servers, databases), and the like, which can be communicatively coupled to the controller 102 via, for example, a communication interface 116. In exemplary embodiments, the controller 102 can process the received signals and can control an operation of the pumps 22a, 22b, the injection member 44, and/or the actuator 90 in response to the signals.

In one exemplary embodiment, the controller 102 can output the actuator control signal to the actuator controller 114 to control a position of the valve member (e.g., shaft 94 and needle 86) to adjust the pressure of the system to control an effect that pressure related hysteresis has an on the system 10 during operation. In exemplary embodiments, the pressure related hysteresis can affect a response rate of the system 10 to requested changes in the pressure (e.g., how quickly the pressure changes from its current value to a requested value). For example, the response rate of the system 10 can be decreased by the effects of the hysteresis such that the system 10 can take longer to reach a requested pressure value than the system 10 normally would if there was no hysteresis in the system 10.

The hysteresis of the system 10 can be associated with a hysteresis band, which refers to a pressure range over which the hysteresis affects the system. The hysteresis band can have an upper boundary and a lower boundary. When the pressure of the system is within the boundaries of the hysteresis band, the hysteresis has a greater effect on a response rate of the system to requested pressure changes. As the pressure changes in the system, the hysteresis band can track the pressure changes such that the pressure values associated with the hysteresis band generally change to follow the pressure of the system. The response rate of the system for pressure changes can be dependent on where the current pressure is with respect to the hysteresis band as well as the magnitude of the pressure change requested and/or the rate at which the pressure is requested to change. Generally the effects of the hysteresis can be more significant larger pressure change and higher rates of change. The hysteresis of the system 10 can be quantified by characterizing the response of the system to pressure changes. Based on the characterization of the response to pressure changes, the pressure range associated with the hysteresis band can be determined.

Figure 8:
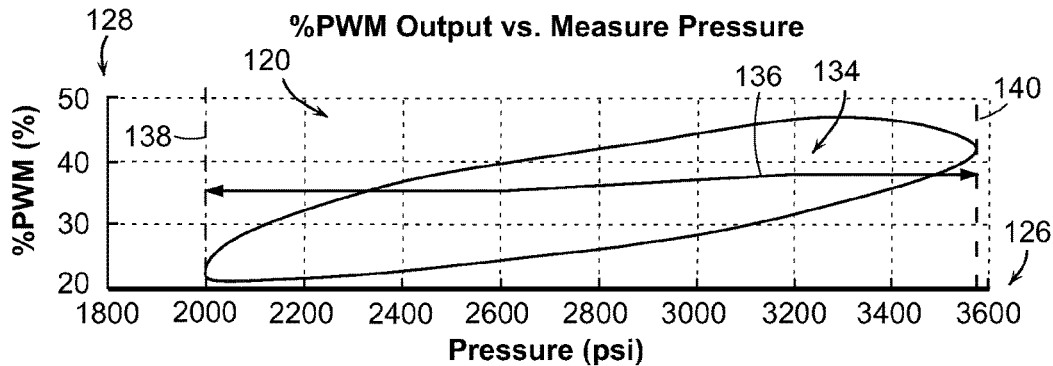
FIG. 8 shows a graph that illustrates an exemplary technique for determining an effect of pressure-related hysteresis in an exemplary embodiment of the pressurized flow system.
Figure 9:
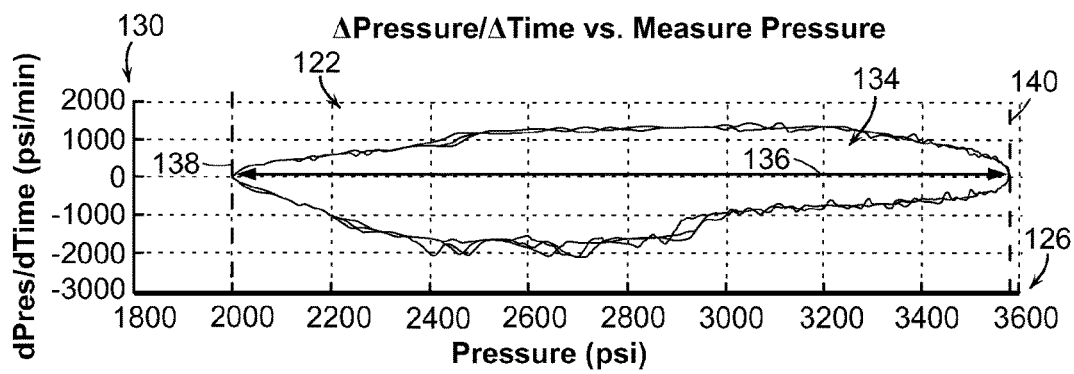
FIG. 9 shows a graph that illustrates another exemplary technique for determining an effect of pressure-related hysteresis in an exemplary embodiment of the pressurized flow system.
Figure 10:
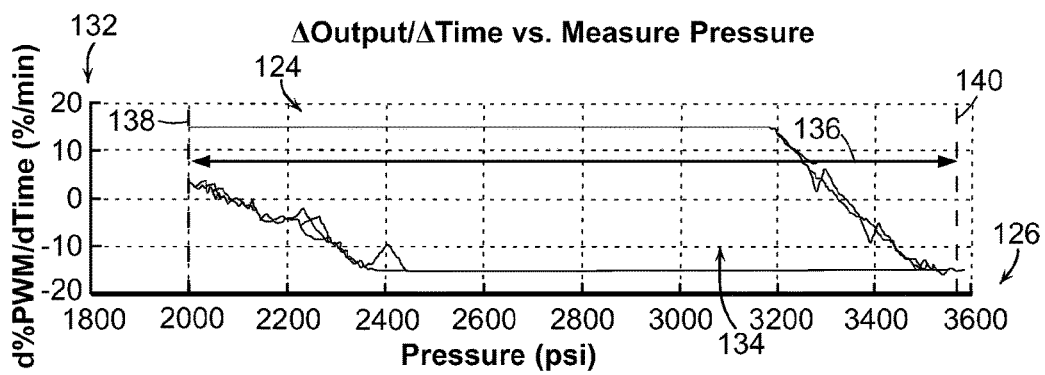
FIG. 10 shows a graph that illustrates yet another exemplary technique for determining an effect of pressure-related hysteresis in an exemplary embodiment of the pressurized flow system.

FIGS. 8-10 show graphs 120, 122, 124, respectively, each of which are illustrative of an exemplary characterization of the hysteresis for an embodiment of the system 10. The graph 120 illustrated in FIG. 8 corresponds to a measurement of the pressure of the system 10 for changes in the actuator control signal implemented using pulse width modulation to adjust the pressure of the system. The graph 122 illustrated in FIG. 9 corresponds to a measurement of the pressure for different requested rates of change for the pressure of the system 10. The graph 124 of FIG. 10 corresponds to a measurement of the pressure of the system 10 for different rates of change of the actuator control signal implemented using pulse width modulation. The x-axis 126 of the graphs 120, 122, 124 corresponds to the pressure of the system 10 measured in pounds per square inch (psi). The y-axis 128 of FIG. 8 corresponds to a duty cycle of a pulse width modulated (PWM) actuator control signal measured as percentage. The y-axis 130 of FIG. 9 corresponds to a rate of change in the pressure measured in psi per minute (psi/min). The y-axis 132 of FIG. 10 corresponds to a rate of change in the PWM actuator control signal measured in percent per minute (%/min).

As shown in FIGS. 8-10, a hysteresis band 134 can be identified in each graph 120, 122, 124, which, for the present embodiment, has a pressure range 136 of about 1,600 psi. For the measurements illustrated in FIGS. 8-10, the lower boundary 138 of the hysteresis band 134 occurs at about 2,000 psi and the upper boundary 140 of the hysteresis band 134 occurs at about 3,600 psi. While the pressure range 136 of the hysteresis band 134 is generally constant, the pressure values of the lower and upper boundaries 138 and 140, respectively, can change based on a current and previous pressure of the system 10. Furthermore, while the hysteresis band 134 has been determined to have a pressure range of 1,600 psi for one embodiment of the system 10, those skilled in the art will recognize that the pressure range 136 of the hysteresis band 134 can be different for this or other embodiments of the system 10 and that the pressure range 136 of the hysteresis band 134 can be determined as described in FIGS. 8-10 or using other techniques.

Figure 11:
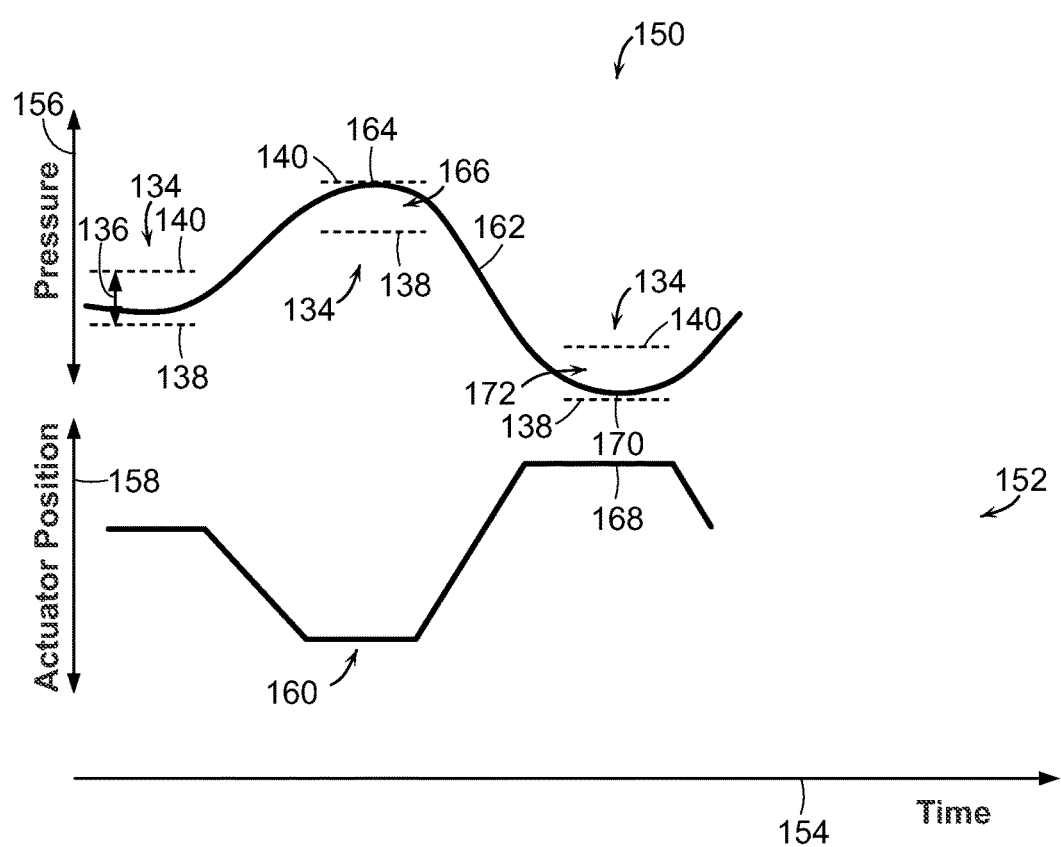
FIG. 11 shows graphs illustrating an exemplary response of the pressure of an exemplary embodiment the system to adjustments in positions of a valve member of an exemplary dynamic pressure regulator.

FIG. 11 shows a graph 150, 152 of an exemplary response of the hysteresis band 134 to changes in pressure resulting from a change in position of the shaft 94 and needle 86 as shown in graph 152 and in accordance with exemplary embodiments of the present disclosure. The x-axis 154 for graphs 150, 152 corresponds to time, the y-axis 156 of the graph 150 corresponds to pressure in psi and the y-axis 158 of the graph 152 corresponds to a distance between the needle 86 and the seat 82 of the actuator 90. A decrease in the distance of shaft 94 and needle 86 from the seat 82 as shown in graph 152 (e.g., an increase in pressure) and an increase in the distance between the shaft 94 and needle 86 from the seat 82 (e.g., a decrease in pressure).

The hysteresis band 134 includes the lower boundary 138 and the upper boundary 140 and has the pressure range 136. As shown in graphs 150, 152, when the distance between the needle and the seat is decreased to a first value 160 in response to a control signal received from the processing device, the pressure 162 of the system 10 responds to the change in position of the needle 86 by increasing to a first pressure value 164. As the pressure 162 increases, the hysteresis band 134 shifts to a first pressure location 166 and the pressure values associated with the lower and upper boundaries 138, 140 increase by a substantially similar amount such that the pressure range of the hysteresis band 134 is unchanged, but the pressure values associated with the hysteresis band 134 change. When the distance between the needle and the seat is increased to a second value 168 in response to the control signal from the processing device, the pressure 162 of the system 10 responds to the change in position of the needle 86 by decreasing to a second pressure value 170. As the pressure 162 decreases, the hysteresis band 134 shifts to a second pressure location 172 and the pressure values associated with the lower and upper boundaries 138, 140 decrease by a substantially similar amount such that the pressure range 136 of the hysteresis band 134 is unchanged, but the pressure values associated with the hysteresis band 134 change. The rate with which the hysteresis band 134 changes its location with respect to the pressure can be based on, for example, a magnitude in the change of pressure, the rate at which the pressure change is requested, previous pressure values of the system 10, and the like.

The pressure related hysteresis associated with embodiments of the system 10 can adversely affect an operation of the system 10 as well as a detection sample component. As one example, in some embodiments, a user may implement a sample detection method for which the user wishes to detect sample components over a pressure gradient. The user can specify a rate of change for the pressure to implement the pressure gradient and can program the system 10 to increase or decrease the pressure of the system 10 at the predetermined rate of change after the sample to be detected has been injected into the system 10. If the rate of change in the pressure is affected by the hysteresis, and the user has not taken into account the effect of the hysteresis, the pressure of the system 10 may not respond as the user expected and/or desired. For example, there may be an unacceptable error between the actual rate of change of the pressure compared to the predetermined rate of change, there may be an unacceptable delay before the pressure increases at the predetermined rate of change such that there is a tracking error between the actual pressure gradient and the predetermined pressure gradient, and/or there may be other error, undesirable effects, or unacceptable effects on the pressure of the system as a result of the hysteresis.

In some instances, the pressure related hysteresis associated with embodiments of the $CO_2$-based chromatography system can be used to advantageously affect an operation of the $CO_2$-based chromatography system as well as a detection sample component. As one example, in some embodiments, a user may implement a sample detection method for which the user wishes to detect sample components over a substantially constant system pressure (e.g., isobaric chromatographic separation). For such methods, the hysteresis of the $CO_2$-based chromatography system can be used to maintain a substantially constant pressure throughout the run.

The adverse effects of the hysteresis can be advantageously minimized and/or the advantageous effects of the hysteresis can be realized for embodiments of the $CO_2$-based chromatography system by setting the pressure of the system to a predetermined location in the hysteresis band. Exemplary embodiments of the $CO_2$-based chromatography system can be configured to control a position of the needle 86 with respect to the seat in the dynamic pressure regulator to manipulate the pressure of the $CO_2$-based chromatography system so that the pressure of the $CO_2$-based chromatography system is positioned at a predetermined location in the hysteresis band.

Figure 12:
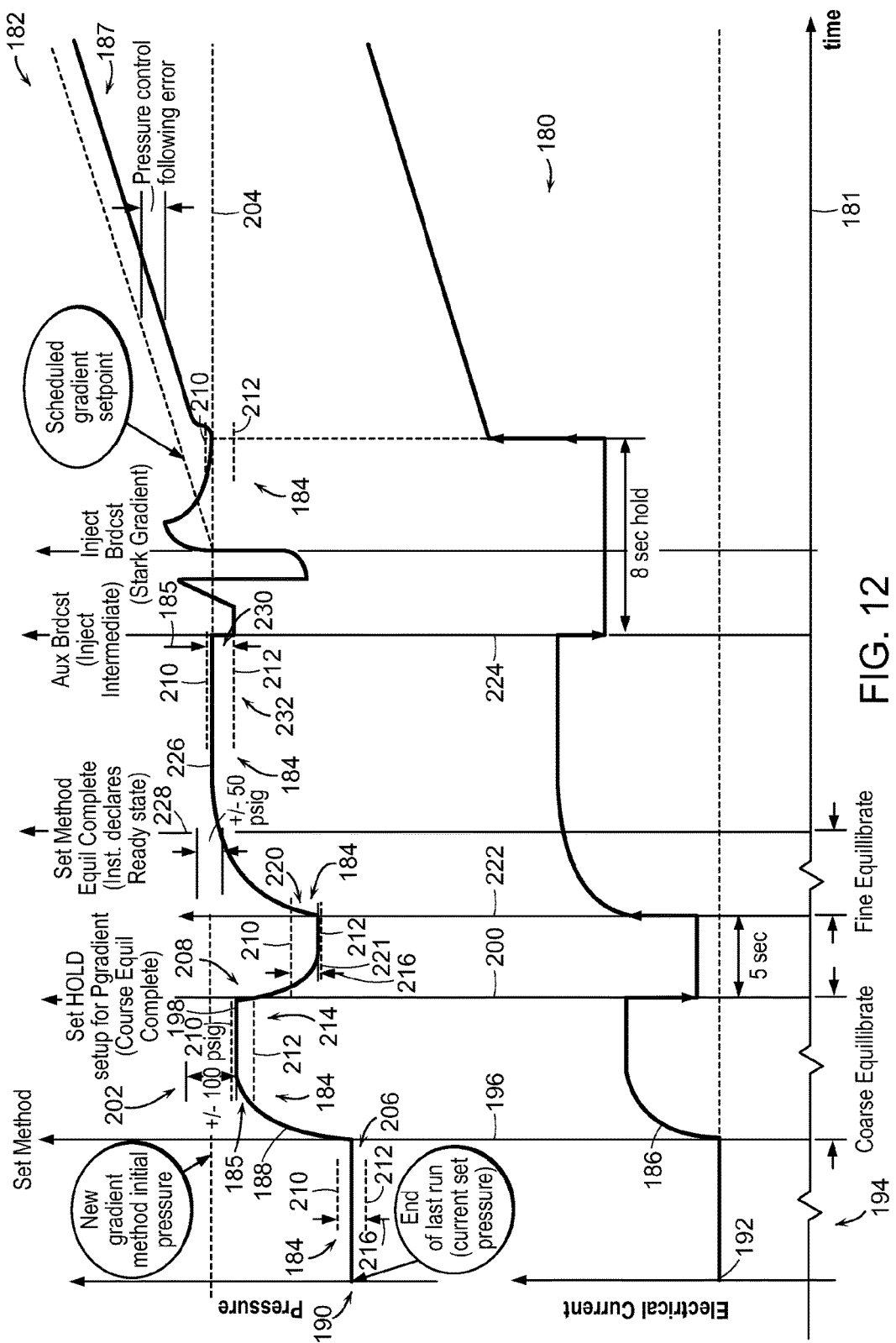
FIG. 12 shows graphs illustrating an exemplary process for controlling an actuator of an exemplary embodiment of the dynamic pressure regulator to set the pressure of an exemplary embodiment of the pressurized flow system to a predetermined location in a hysteresis band.

FIG. 12 shows graphs 180, 182 illustrating an exemplary process for controlling the actuator 90 of the dynamic pressure regulator 57 to set the pressure to a predetermined location in a hysteresis band 184. The graph 180 represents an electrical current 186 being supplied to the actuator 90 over time 181 and the graph 182 represents a pressure 188 of the system 10 that corresponds to the electric current 186 being supplied to the actuator 90. The pressure 188 of the system 10 and the electrical current 186 supplied to the actuator 90 can have initial conditions 190, 192, respectively, which can correspond to the pressure 188 of the system 10 and the electrical current 186 of supplied to the actuator 90 upon activation of the system 10, after completion of a previous sample run (e.g., a previous sample detection), or after completion of a system calibration or diagnostic process. In exemplary embodiments, a change in pressure of the system 10 can exceed a pressure range 185 of the hysteresis band to adjust a pressure value of the system beyond an upper or lower boundary of the hysteresis band 184 to set the pressure to the upper or lower boundary, respectively, of the hysteresis band 184.

At time 194, the relationship between the system pressure 188 and the hysteresis band 184 can be uncertain. A new sample run can be initiated for which a sample is to be chromatographically separated while being exposed to a pressure gradient 187 and the system can be configured to minimize the effect of the hysteresis on the pressure gradient 187 by setting 10 the system pressure 188 to a predetermined location in the hysteresis band 184. At time 196, the new sample run can be initiated and the electric current 186 to the actuator can be increased to position the needle 86 closer to the seat 82 to increase the pressure 188 as shown. The pressure 188 can be increased to a pressure value 198 at time 200 that is within a predetermined pressure range 202 to a pressure value 204 that corresponds to an initial pressure of the pressure gradient 187 for the sample run. The change in pressure to the pressure value 198 can be greater than the pressure range 185 of the hysteresis band 184 and/or can exceed an upper boundary 210 of the hysteresis band 184 to set the pressure of the system at the upper boundary 210 of the hysteresis band 184. The change in pressure over the time period between the times 196 and 200 can be referred to as a course equilibrate period. The hysteresis band 184 can shift with the increase in pressure 188 from its initial undetermined location 206 to a first location 208 with respect to pressure. For example, the upper boundary 210 of the hysteresis band 184 can shift to the pressure value 198 and the lower boundary 212 of the hysteresis band 184 can shift by a substantially similar amount to a first lower boundary pressure value 214 such that a pressure range 185 of the hysteresis band 184 remains generally constant. After the pressure 188 has reached the pressure value 198, the electric current 186 can be decreased at time 200 to position the needle 86 further away from the seat 82 to decrease the pressure of the system 10 to a pressure value 221. The change in the pressure of the system from the pressure value 198 to the pressure value 221 can exceed the pressure range 185 of the hysteresis band 184 and/or can exceed the pressure value associated with the lower boundary 212 of the hysteresis band. The hysteresis band 184 can shift to a second location 220 with respect to pressure in preparation for setting the pressure 188 approximately to the pressure value 204 pressure. At the second location 220, the pressure 188 of the system can be set at the lower boundary 212 of the hysteresis band 184.

Between times 222 and 224, the pressure 188 can be increased to a pressure value 226 that is within a predetermined pressure range 228 to the pressure value 200. The time period between the times 222 and 224 can be referred to as a fine equilibrate period because the pressure range 228 is smaller than the pressure range 202 of the course equilibrate. For example, the course equilibrate period can set the pressure 188 to within approximately 100 psi of the pressure value 204 and the fine equilibrate period can set the pressure to within approximately 50 psi of the pressure value 204. The change in the pressure 188 from the pressure value 221 to the pressure value 226 can be greater than the pressure range 185 of the hysteresis band and/or can exceed the pressure value associated with the upper boundary 210 of the hysteresis band 184. In some embodiments, the pressure value 226 can be less than, substantially equal to, or greater than the pressure value 204. In exemplary embodiments, the pressure 188 can be increase after a predetermined time period and/or in response to a command signal. The hysteresis band 184 can shift with the increase in the pressure 188 from the second location 220 to a third location 230 with respect to pressure. For example, the upper boundary 210 of the hysteresis band 184 can shift to the pressure value 226 (e.g., the pressure 188 of the system is set at the upper boundary 210) and the lower boundary 212 of the hysteresis band 184 can shift by a substantially similar amount to a lower boundary pressure value 232 such that the pressure range 185 of the hysteresis band 184 remains generally constant.

Once the pressure 188 is set approximately to the pressure value 204 (e.g., the pressure value 226), the system pressure is set to a predetermined location in the hysteresis band (e.g., at the upper boundary of the hysteresis band) and is ready to process a sample. The injection of the sample into the solvent stream (e.g., the mobile phase) can create a pressure disturbance in the system 10, which can disrupt the position of the pressure in the hysteresis band and cause sample detection errors due to the effects of the hysteresis. To prevent or reduce the effect of the disturbance caused by the injection, the system 10 can implement an injection procedure to ensure that the pressure 188 of the system 10 is at the predetermined location with respect to the hysteresis band 184 after the injection and disturbance from the injection settles.

In the injection procedure, a pre-injection command signal can be issued at time 224 in preparation for receiving an injection of the sample. In some embodiments, the pre-injection command signal can be issued by the controller 102 (e.g., a processing device) of the control system 100. In some embodiments, the pre-injection command signal can be issued by a processing device of a computing device that is in communication with the system 10 (e.g., in communication with the controller 102). Issuance of the pre-injection command causes the processing device to control the actuator 90 to position the needle 86 away from the seat 82 to decrease the pressure 188 in preparation for receiving the injection of the sample. The pressure 188 is decrease by an amount that is exceeds the lower boundary 212 of the hysteresis band 184 to shift the hysteresis band 184 so that a pressure value associated with the upper boundary 210 is less than the pressure value 204.

After the injection has been received and the pressure disturbance associated with the injection has settled, the system 10 pressure can be increased to set the initial pressure value for the pressure gradient 187 to be within the pressure range 228 (e.g., to approximately the pressure value 204) and to set the pressure to the upper boundary 212 (e.g., a predetermined location) of the hysteresis band 184. By decreasing the pressure before the injection of the sample and subsequently increasing the pressure after the disturbance from the injection has settled to within the pressure range 228 of the pressure value 200, exemplary embodiments ensure that the pressure is set to the upper boundary of the hysteresis band and that the pressure of the system 10 is approximately the pressure value 204 (e.g., within the pressure range 228) before the pressure gradient 187 is implemented.

The system 10 can be configured to increase the pressure after the injection based an a predetermined time period and/or a post injection control signal. For example, experiments can be performed to determine a duration of the disturbance introduced to the system after an injection and the control system can be configured to increase the pressure of the system after a predetermined time has elapsed from receiving the pre-injection control signal. For example, exemplary embodiments can wait for approximately two (2) seconds to about ten (10) second or approximately five (5) seconds or more. The duration of the disturbance can be measured based on how long the disturbance takes to settle to within an acceptable pressure range such that the operation of the system 10 can perform sample separation and detection without substantial effects from the disturbance.

By setting the pressure to the upper boundary of the hysteresis band, the system 10 can eliminate or minimize the effect the hysteresis has on the pressure gradient 187 since the effect of the hysteresis at pressures greater than the upper boundary of the hysteresis band 184 are minimal. Using this approach, the pressure of the system 10 can be consistently controlled for sample runs in which a pressure gradient 187 is used. There can be some tracking error 236 associated between the ideal pressure values and the actual pressure values of the pressure gradient 187, but this tracking error can be considered and compensated by the system 10 since the response of the system to the pressure gradient 187 is consistent for multiple sample runs. While the present embodiment is illustrative of a positive pressure gradient, those skilled in the art will recognize that a similar procedure can be implemented for a negative pressure gradient by setting the pressure of the system 10 to the lower boundary of the hysteresis band.

Figure 13:
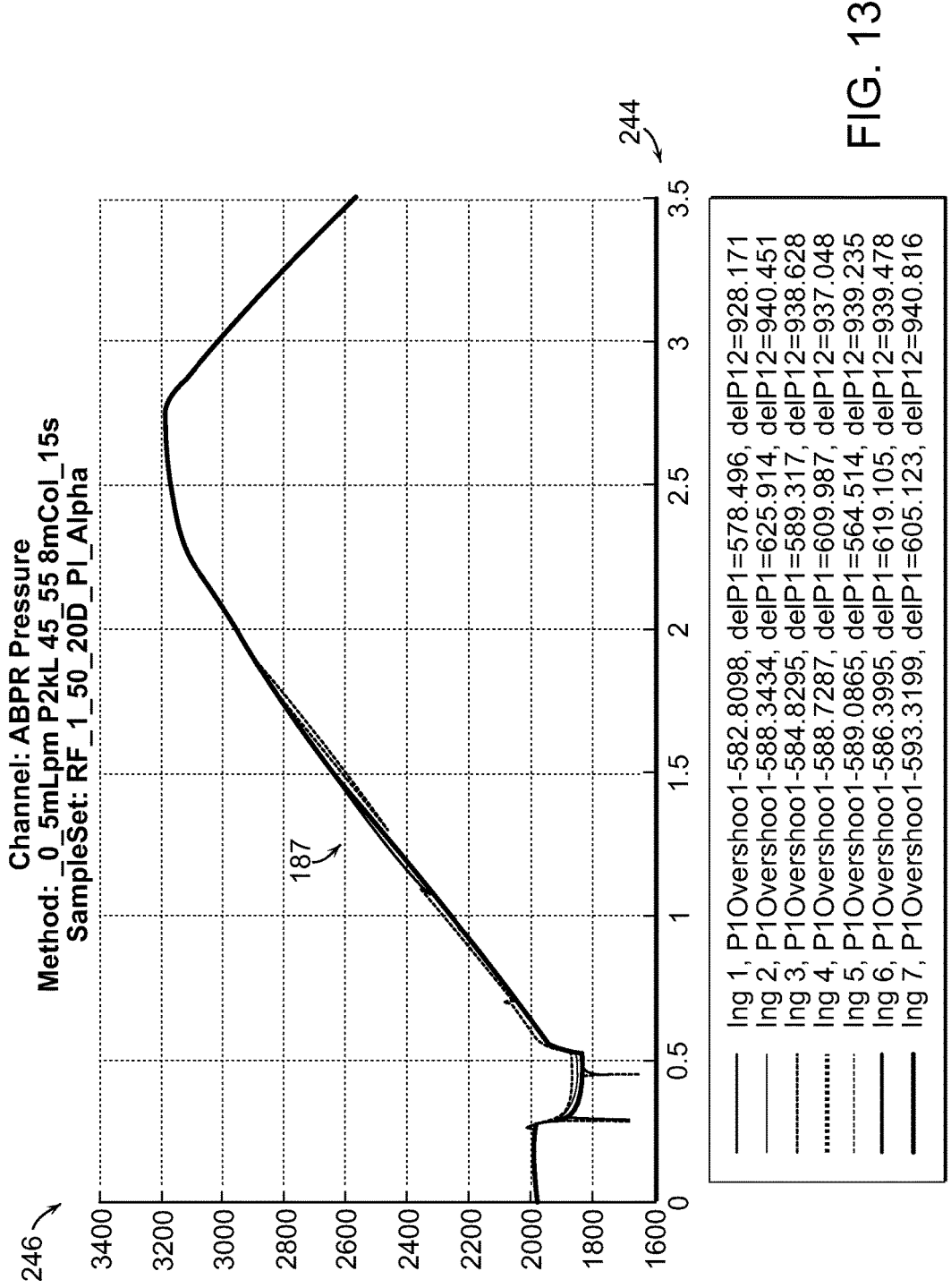
FIG. 13 shows a graph corresponding to a pressure gradient for exemplary sample runs using the process of FIG. 12.

FIG. 13 shows a graph 240 of the pressure gradient 187 for exemplary sample runs using the above procedure of FIG. 12. The x-axis 244 of the graph corresponds to time in minutes and the y-axis 246 of the graph corresponds to pressure in psi. As shown in FIG. 13, the pressure gradient 187 is substantially consistent across different sample runs. As a result, users of the system 10 can obtain consistent sample measurements without substantial variations in the pressure gradient 187 due to the hysteresis of the system 10 and/or a disturbance from the injection of the sample.

Figure 14:
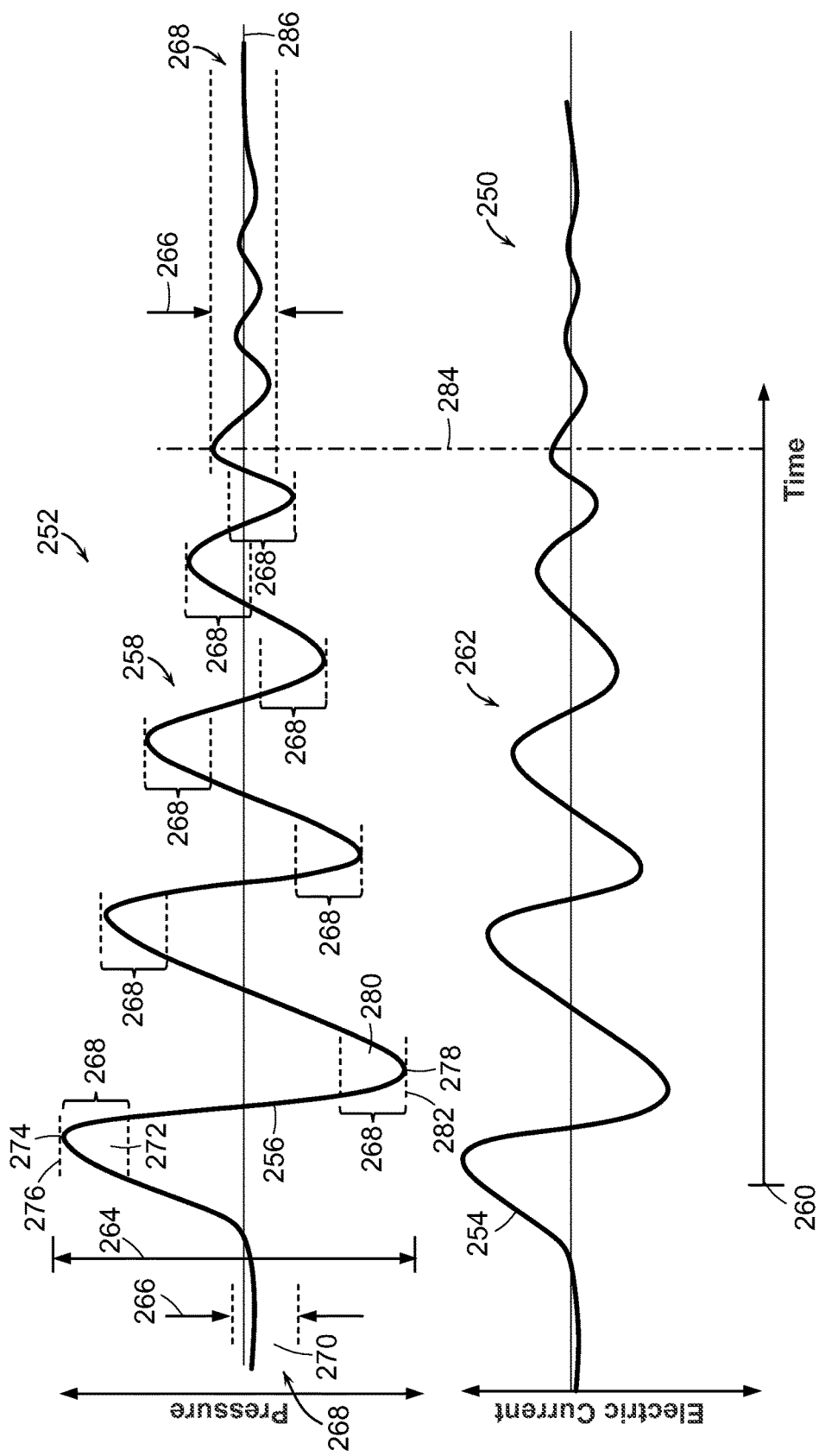
FIG. 14 shows graphs illustrating another exemplary process for controlling an actuator of an exemplary embodiment of the dynamic pressure regulator to set the pressure of an exemplar embodiment of the pressurized flow system to a predetermined location in the hysteresis band.

FIG. 14 shows graphs 250, 252 illustrating another exemplary process for controlling the actuator 90 of the dynamic pressure regulator to set the pressure to a predetermined location in the hysteresis band. The graph 250 represents an electrical current 254 being supplied to the actuator over time and the graph 252 represents a pressure 256 of the system 10 that corresponds to the electric current 254 being supplied to the actuator 90. In the present embodiment, the electric current 254 can be a periodic decaying signal, such as a decaying sine wave. While a decaying sine wave is illustrated in this embodiment, those skilled in the art will recognize that other periodic or aperiodic signals having alternating peaks can be used, e.g., a decaying triangle wave, or other decaying signal having alternating peaks. The electric current 254 of the actuator 90 can correspond to a position of the needle with respect to the seat such that increasing current 254 moves the needle 86 towards from the seat 82 (e.g., increases pressure) and decreasing current 254 moves the needle 86 away from the seat 82 (e.g., decreasing pressure). The pressure 256 of the system can generally correlate to the decaying periodic electrical current signal 254 such that the pressure 256 of the system 10 generally has a decaying periodic waveform 258 that is proportional to the decaying periodic signal of the electric current 254.

As shown in FIG. 14, at time 260, the decaying periodic waveform 258 generated by the decaying periodic electric current 262 can have a peak-to-peak amplitude 264 that is greater than a pressure range 266 of a hysteresis band 268 so that a location of the hysteresis band 268 initially follows the decaying periodic waveform 258 of the pressure 256. For example, the hysteresis band 268 can shift from a first location 270 to a second position 272 with respect to pressure. The second location 272 can correspond to a first peak 274 of the decaying periodic waveform 258 such that the upper boundary 276 of the hysteresis band 268 is substantial equal to the pressure value associated with the first peak 274. As the pressure 256 decreases from the first peak 274 to a second peak 278, the hysteresis band 268 can shift towards the second peak 278 to assume a third location 280 at which the lower boundary 282 of the hysteresis band 268 is substantially equal to the pressure value associated with the second peak 278.

Thus, the hysteresis band 268 can shift between the alternating peaks of the decaying periodic waveform 258 of the pressure 256 until the peak-to-peak amplitude 264 of the decaying periodic waveform 258 is less than or equal to the pressure range 266 of the hysteresis band 268, at which time (e.g., time 284) the location of the hysteresis band 268 remains generally constant. As the decaying periodic waveform 258 of the pressure 256 continues to decay in response to the decaying periodic signal of the electric current 254, the pressure 256 of the system stays within the upper and lower boundaries 276, 282 of the hysteresis band 268 and settles approximately at a center 286 of the hysteresis band 268. Thus, the present embodiment can be implemented to set the pressure of the system to about the center (e.g., a predetermined location) in the hysteresis band 268.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

The invention claimed is:

1. A chromatography or extraction system, the system comprising:
    a solvent delivery subsystem;
    a sample delivery subsystem;
    a sample separation subsystem;
    a flow path fluidically connecting the solvent delivery subsystem, the sample delivery subsystem, and the sample separation subsystem;
    a valve in the flow path configured to adjust pressure of the system, wherein the pressure exhibits hysteresis with respect to valve position; and
    a controller in communication with the valve, the controller configured to locate an upper boundary and a lower boundary of the hysteresis and to set the pressure by adjusting the valve such that the pressure is set to the upper boundary of the hysteresis.

2. The system of claim 1, wherein the controller is configured to set the pressure such that the pressure is set to the upper boundary of the hysteresis by
    closing the valve to set the pressure.

3. The system of claim 1, wherein the controller is configured to set the pressure such that the pressure is set to the upper boundary of the hysteresis by
    (i) opening the valve to set a preliminary pressure, then
    (ii) closing the valve to set the pressure.

4. The system of claim 3, wherein the preliminary pressure is at the lower boundary of the hysteresis.

5. The system of claim 3, wherein the controller is configured to control the valve to transition from the preliminary pressure to the set pressure after a predetermined time period has elapsed.

6. The system of claim 1, wherein the controller is configured to set the pressure such that the pressure is set to the upper boundary of the hysteresis by
    (i) closing the valve to set a first preliminary pressure; then
    (ii) opening the valve to set a second preliminary pressure; then
    (iii) closing the valve to set the pressure.

7. The system of claim 6, wherein the first preliminary pressure and the set pressure are substantially equal.

8. The system of claim 6, wherein the first preliminary pressure is at the upper boundary of the hysteresis and the second preliminary pressure is at the lower boundary of the hysteresis.

9. The system of claim 1, wherein the controller sets the pressure such that the pressure is set to the upper boundary of the hysteresis before a sample is injected into the system.

10. The system of claim 1, wherein the valve comprises an actuator in communication with a valve member and the actuator adjusts a position of the valve member to adjust the pressure of the system.

11. The system of claim 10, wherein the actuator and valve member are components of a dynamic pressure regulator of the system.

12. The system of claim 10, wherein the actuator comprises at least one of a solenoid and a voice coil.

13. The system of claim 1, wherein the controller adjusts the valve in response to a command signal.

14. The system of claim 1, wherein the system is a $CO_2$-based chromatography system.

* * * * *